(12) United States Patent
Garcia et al.

(10) Patent No.: US 11,925,166 B2
(45) Date of Patent: Mar. 12, 2024

(54) CACAO CELL SUSPENSION PROTOCOL

(71) Applicant: Mars, Incorporated, McLean, VA (US)

(72) Inventors: Claudia Yanet Garcia, Itabuna (BR); Dahyana Britto, Ilhéus (BR); Jean-Philippe Marelli, Fort Lauderdale, FL (US); Lidiane Dos Santos Silva, Itajuípe (BR)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 17/617,215

(22) PCT Filed: Jun. 5, 2020

(86) PCT No.: PCT/US2020/036356
§ 371 (c)(1),
(2) Date: Dec. 7, 2021

(87) PCT Pub. No.: WO2020/247771
PCT Pub. Date: Dec. 10, 2020

(65) Prior Publication Data
US 2022/0232790 A1    Jul. 28, 2022

Related U.S. Application Data

(60) Provisional application No. 62/858,571, filed on Jun. 7, 2019.

(51) Int. Cl.
*A01H 6/60* (2018.01)
*A01H 4/00* (2006.01)
*A01H 5/10* (2018.01)
*A01H 5/12* (2018.01)

(52) U.S. Cl.
CPC ............... *A01H 6/60* (2018.05); *A01H 4/002* (2021.01); *A01H 4/005* (2013.01); *A01H 5/10* (2013.01)

(58) Field of Classification Search
CPC .............. A01H 6/60; A01H 4/005; A01H 5/12
See application file for complete search history.

(56) References Cited

U.S. PATENT DOCUMENTS

| | | | |
|---|---|---|---|
| 4,306,022 A | 12/1981 | Kinsella et al. | |
| 4,545,147 A * | 10/1985 | Janick | A01H 4/00 435/430.1 |
| 5,312,801 A * | 5/1994 | Sondahl | A01H 4/00 435/430.1 |
| 8,568,798 B2 * | 10/2013 | Venkatramesh | A61P 9/10 424/769 |
| 9,428,759 B2 | 8/2016 | Rengifo | |
| 2017/0121722 A1 | 5/2017 | Anand et al. | |

FOREIGN PATENT DOCUMENTS

| | | |
|---|---|---|
| CN | 102414312 A | 4/2012 |
| CN | 103237457 A | 8/2013 |
| WO | 2010114567 A1 | 10/2010 |
| WO | WO-2010114567 A1 | 10/2010 |

OTHER PUBLICATIONS

Moyer et al. "Regeneration of *Coronilla varia* L. (crownvetch) plants from callus culture," Plant Cell Tissue Organ Culture 3: 143-148 (1984).*
Wen et al. "Fatty Acid Composition of Suspension Cell Cultures of Theobroma Cacao are Altered by Culture Conditions," Journal of Food Science, vol. 57, No. 6, pp. 1452-1453,1992.*
Gallego et al., (2018). "Transcriptomic analyses of cacao cell suspensions in light and dark provide target genes for controlled flavonoid production," Scientific reports, 8:13575, 14 pages.
Gamborg et al., (1968). "Nutrient requirements of suspension cultures of soybean root cells," Experimental cell research, 50:151-158.
Greathouse et al., (1971). "The Shoot-Growth Rhythm of a Tropical Tree, *Theobroma cacao*," American journal of botany, 58:281-286.
International Search Report and Written Opinion received for International Patent Application No. PCT/US2020/36356 dated Oct. 21, 2020, 13 pages.
Plantigen Himedia, (2017). "Woody Plant Medium," available online at <https://himedialabs.com/TD/PT026.pdf>, 2 pages.
Rojas et al., (2008). "Total polyphenol analysis of mature seeds and cell cultures of some Colombian cacao varieties," Actualidades Biologicas, 30:117-123.
Rua et al., (2017). "A rational approach for the improvement of biomass production and lipid profile in cacao cell suspensions," Bioprocess and biosystems engineering, 10:1479-1492, 14 pages.
Leathers and Scragg, "The Effect of Different Temperatures on the Gorwth, Lipid Content and Fatty Acid Compositions of Theobroma Cacao Cell Suspensiont", Plant Science 62.2 (1989): 217-227.
Database Agris [Online] Food and Agriculture Organization of the United Nations; Jan. 2001 (Jan. 1, 2001), "Morphology, histology and cytology of enhanced axillary bud formation and production of cell suspension culture of *Theobroma cacao* L. in vitro", Database accession No. PH2001100234.
Ndoumou D. Omokolo et al., "Phenol content, acidic peroxidase and IAA-oxidase during somatic embryogenesis in *Theobroma cacao* L.", Biologia Plantarum, 39(3): 337-347, Apr. 1, 1997 (Apr. 1, 1997), XP93020308, Retrieved from the Internet: https/a://link.springer.com/content/pdf/ 10.1023/A:1001041222799.pdf.

(Continued)

*Primary Examiner* — Susan McCormick Ewoldt

(57) ABSTRACT

Provided herein are methods for establishing *Theobroma* cell suspension cultures using young leaves as a source of explants. Also provided are induction, proliferation, and suspension media used for producing *Theobroma* cell suspension cultures. These methods and media may be useful for producing secondary metabolites in *Theobroma*, as well as for isolating virus particles associated with *Theobroma* diseases.

13 Claims, 7 Drawing Sheets

(56) References Cited

OTHER PUBLICATIONS

Wang, Junli et al., "An efficient callus proliferation protocol and rhaponticin accumulation of *Rheum franzenbachii* Munt., a medicinal plant", Journal of Plant Biochemistry and Biotechnology, 20(2): 252-257, Jul. 2011, Retrieved from the Internet: https/a://link.springer.com/content/pdf/ 10.1007/s13562-011-0055-4.pdf.
Abraham, (2009). "Somatic Embryogenesis of Cacao Cotyledon Explants," Tropical Agriculture Information, 3:2-4. English abstract.
McCown et al., (1981). "Abstract 394: Woody Plant Medium (WPM)—A Mineral Nutrient Formulation for Microculture of Woody Plant Species," HortScience, 16(3):453.
Murashige et al., (1962). "A Revised Medium for Rapid Growth and Bio Assays with Tobacco Tissue Cultures," Physiologia Plantarum, 15:473-497.
Parra et al., (2017). "Biochemical precursor effects on the fatty acid production in cell suspension cultures of *Theobroma cacao* L," Plant Physiology and Biochemistry, 111:59-66.
Tsai et al., (1981). "Initiation and growth of callus and cell suspensions of *Theobroma cacao* L.," Annals of Botany 48:549-557.

\* cited by examiner

CACAO CELL SUSPENSION PROTOCOL

CROSS REFERENCE TO RELATED APPLICATIONS

This application is a national stage application under 35 U.S.C. § 371 of International Application No. PCT/US2020/036356, filed internationally on Jun. 5, 2020, which claims priority to and the benefit of U.S. Provisional Patent Application No. 62/858,571, filed on Jun. 7, 2019, the disclosures of which are incorporated herein by reference in their entireties.

FIELD

The present disclosure relates generally to plant cell cultures, and more specifically to methods of establishing *Theobroma* cell suspension cultures.

BACKGROUND

*Theobroma* is a genus of flowering plants in the mallow family Malvaceae. *Theobroma* contains roughly twenty species of small understory trees native to the tropical forests of Central and South America. *Theobroma cacao* may be used for making chocolate.

Plant cell suspension culture is a process by which plant cells are grown free floating in culture medium. A *Theobroma* cell suspension culture is generally amenable to large-scale production of *Theobroma* secondary metabolites such as theobromine. Previous attempts of establishing *Theobroma* cell suspension cultures have largely relied on using cotyledons or developing seeds as explant materials. See e.g. Tsai and Kinsella, *Annals of Botany* 48.4 (1981): 549-558; Leathers and Scragg, *Plant science* 62.2 (1989): 217-227; Rojas et al., *Actualidades Biológicas* 30.89 (2008): 117-123; Paira et al., *Plant physiology and biochemistry* 111 (2017): 59-66; Rúa et al., *Bioprocess and biosystems engineering* 40.10 (2017): 1479-1492; Gallego et al., *Scientific reports* 8.1 (2018): 13575. Obtaining these kinds of explants on a commercial production scale, however, can be time-consuming and labor-intensive, and may overall increase the costs of commercial production of *Theobroma* related products.

Accordingly, there is a need for improved methods that provide efficient and effective protocols for establishing *Theobroma* cell suspension cultures.

BRIEF SUMMARY

Provided herein are methods for establishing *Theobroma* cell suspension cultures using young leaves as a source of explants, suitable for production of *Theobroma* secondary metabolites, as well as for isolation of viruses associated with *Theobroma* diseases. Also provided herein are growth media used in the methods.

In one aspect, provided herein is a method for preparing a *Theobroma* cell suspension culture by: obtaining an explant from a *Theobroma* leaf; sterilizing the explant; inducing friable callus from the explant on a callus induction medium; proliferating the induced callus on a callus proliferation medium; and suspending the proliferated callus in a suspension medium, the callus induction medium includes a base plant medium; 1-naphthaleneacetic acid (NAA) and 6-benzylaminopurine (BAP). In certain variations, the 1-naphthaleneacetic acid (NAA) is present at a concentration of 0.5 mg/L to 5 mg/L; and the 6-benzylaminopurine (BAP) is present at a concentration of 0.5 mg/L to 5 mg/L.

In some embodiments, the sterilization includes contacting the explant in a hypochlorite solution under vacuum. In some embodiments, the callus proliferation medium includes a base plant medium; and glutamine. In some embodiments, the suspension medium includes a base plant medium; and L-glycine. In some embodiments, the induction of friable callus is obtained after a photoperiod of 16 hours of light and 8 hours of dark. In some embodiments, provided is a *Theobroma* cell suspension culture produced by the foregoing methods.

In another aspect, provided herein is a method for producing a *Theobroma* secondary metabolite by: obtaining an explant from a *Theobroma* leaf; sterilizing the explant; inducing friable callus from the explant on a callus induction medium; proliferating the transformed friable callus on a callus proliferation medium; suspending the proliferated callus in a suspension medium; and recovering a secondary metabolite from the suspension medium. In some embodiments, the callus induction medium includes a base plant medium; 1-naphthaleneacetic acid (NAA) and 6-benzylaminopurine (BAP). In certain variations, the 1-naphthaleneacetic acid (NAA) is present at a concentration of 0.5 mg/L to 5 mg/L, and the 6-benzylaminopurine (BAP) is present at a concentration of 0.5 mg/L to 5 mg/L.

In some variations, the method for producing a *Theobroma* secondary metabolite further comprises transforming the induced callus with an expressible transgene that encodes a product in the biosynthetic pathway of the secondary metabolite. In some embodiments, the transformation is achieved by particle bombardment or by *Agrobacterium* mediation. In some embodiments, the secondary metabolite is a phenol, a flavonoid, a methylxanthine, or a fatty acid. In some embodiments, the *Theobroma* is *Theobroma cacao*, *Theobroma grandiflorum*, or *Theobroma bicolor*. In some embodiments, the sterilization includes contacting the explant in a hypochlorite solution under vacuum. In some embodiments, the callus proliferation medium includes a base plant medium; and glutamine. In some embodiments, the suspension medium includes a base plant medium; and L-glycine. In some embodiments, the induction of friable callus is obtained after a photoperiod of 16 hours of light and 8 hours of dark.

In some embodiments that may be combined with any of the foregoing embodiments and variations, the method further includes co-cultivating the cell suspension with one or more viruses. In some embodiments, the one or more viruses include the cacao swollen shoot virus (CSSV). In some embodiments, provided is a *Theobroma* secondary metabolite produced by the foregoing methods.

In yet another aspect, provided herein is a callus induction medium for inducing friable callus from *Theobroma* leaf explants, including: a base plant medium; 1-naphthaleneacetic acid (NAA) and 6-benzylaminopurine (BAP). In certain variations, the 1-naphthaleneacetic acid (NAA) is present at a concentration of 0.5 mg/L to 5 mg/L, and the 6-benzylaminopurine (BAP) is present at a concentration of 0.5 mg/L to 5 mg/L. In other variations, the callus induction medium further includes a vitamin mixture.

In still another aspect, provided herein is a callus proliferation medium for proliferating friable callus induced from *Theobroma* leaf explants, including: a base plant medium, and tidiazuron (TDZ) at a concentration of 1 mg/L to 5 mg/L. In some variations, the callus induction medium further includes a vitamin mixture.

DESCRIPTION OF THE FIGURES

With reference to FIGS. 5-7, BAP is 6-benzylaminopurine; and NAA is 1-naphthaleneacetic acid.

DETAILED DESCRIPTION

Figure 1:
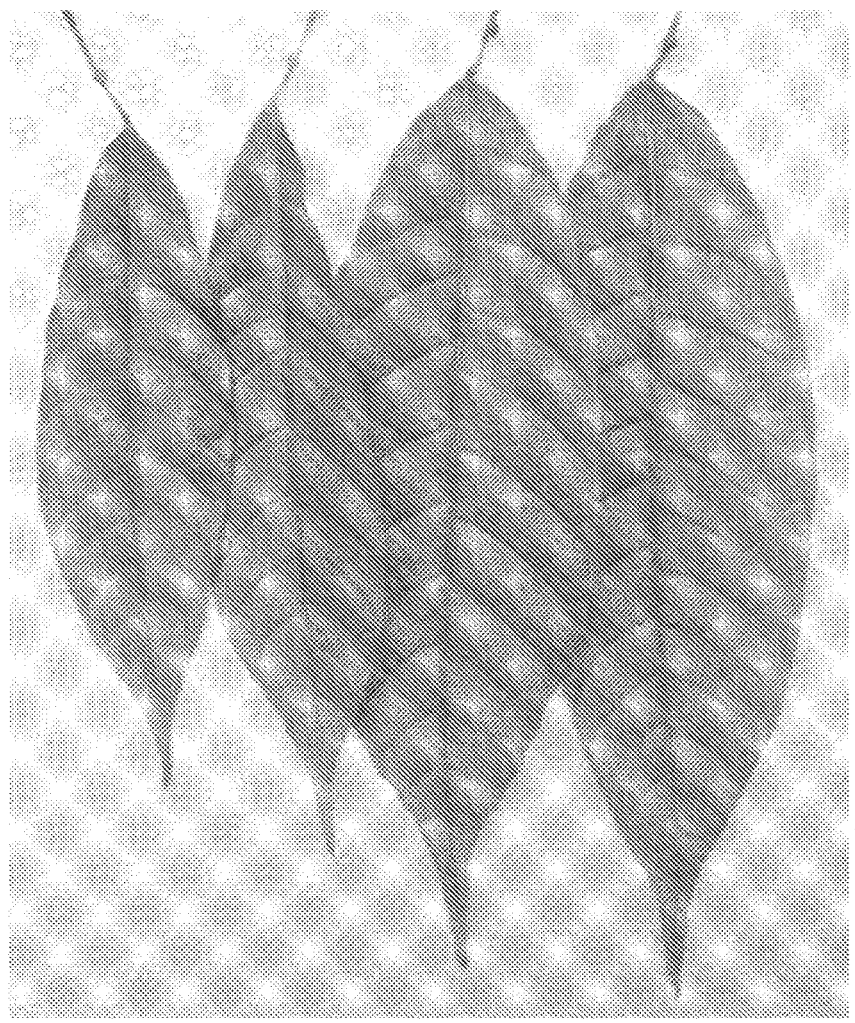
FIG. 1 shows a photograph of representative leaves for obtaining explants.

The following description sets forth exemplary compositions, systems, methods, parameters and the like. It should be recognized, however, that such description is not intended as a limitation on the scope of the present disclosure but is instead provided as a description of exemplary embodiments.

Methods for Establishing *Theobroma* Cell Suspension Cultures

In one aspect, provided herein is method for preparing a *Theobroma* cell suspension culture by: obtaining an explant from a *Theobroma* leaf; sterilizing the explant; inducing friable callus from the explant on a callus induction medium; proliferating the induced callus on a callus proliferation medium; and suspending the proliferated callus in a suspension medium.

*Theobroma* is a genus of flowering plants in the mallow family Malvaceae. Suitable examples of the *Theobroma* species for use in the methods described herein include, for example, *Theobroma cacao, Theobroma grandiflorum, Theobroma bicolor, Theobroma angustifolium, Theobroma canumanense, Theobroma mammosum, Theobroma microcarpum, Theobroma obovatum, Theobroma simiarum, Theobroma speciosum, Theobroma stipulatum, Theobroma subincanum,* or *Theobroma sylvestre*. In one variation, the *Theobroma* is *Theobroma cacao*. In another variation, the *Theobroma* is *Theobroma grandiflorum*. In yet another variation, the *Theobroma* is *Theobroma bicolor.*

Leaf Explants and Sterilization Thereof

The explant is a piece of tissue taken from a donor plant for culturing. Previous attempts of establishing *Theobroma* cell suspension cultures have largely relied on using cotyledons or developing seeds as explant materials. Obtaining these types of explants is time-consuming and labor-intensive because hand pollination is required to produce seed. However, once obtained, cotyledons or developing seeds are relatively easy to sterilize for tissue culture because they are grown inside of a fruit shielded from the external environment. In contrast, since leaves are exposed to the external environment, they are typically harder to sterilize, which is one of the reasons for limiting their use as a source of explants for tissue culture.

In certain embodiments, provided is a method of sterilizing *Theobroma* leaves to make them suitable for use as explants in tissue culture. In some embodiments, leaves are cleaned with soap, rinsed with distilled sterile water, and cut into pieces. In some embodiments, the cut leaf pieces are disinfected by immersion in ethanol, rinsed with sterile water, and immersed in a hypochlorite solution under vacuum. In some embodiments, after disinfection, the leaves may be used in a variety of protocols.

In some embodiments, the ethanol is provided in a 70%-95% ethanol solution.

In other embodiments, the hypochlorite solution comprises calcium hypochlorite. In some embodiments, the calcium hypochlorite solution is at a concentration of between 0.5% and 10%, or between 0.5% and 5%; or about 1%, about 2%, about 3%, about 4%, about 5%, about 6%, about 7%, about 8%, about 9%, or about 10%.

In yet other embodiments, the hypochlorite solution comprises sodium hypochlorite. In some embodiments, the sodium hypochlorite solution is at a concentration of between 5% and 30%; or about 5%, about 10%, about 15%, about 20%, about 25%, or about 30%.

In yet other embodiments, the cut leaf pieces are immersed in a hypochlorite solution under vacuum at between 10 kPa and 100 kPa; or about 10 kilopascal, about 20 kPa, about 30 kPa, about 40 kPa, about 50 kPa, about 60 kPa, about 70 kPa, about 80 kPa, about 90 kPa, or about 100 kPa. In some embodiments, the vacuum and sterilization protocol may be adapted to prepare other cacao samples for protocols such as root formation.

Induction of Friable Callus

A callus is a growing mass of unorganized plant parenchyma cells. Callus is formed by the proliferation of the parent tissue. Morphologically speaking, callus cultures are typically classified as being either friable or compact. Friable callus anatomically is made up of large loosely arranged cells with intercellular spaces. Friable callus is fragile, easily breaks up, and is suitable for suspension culture, where the tissue can be dispersed by mechanical agitation. In contrast, compact callus is hard and anatomically made up of compactly arranged small cells without intercellular spaces. Compact callus does not fall apart easily. See generally Kumar, et al. "Callus Induction." *Plant Biotechnology, Volume* 1. Apple Academic Press, 2017. 143-159.

In some embodiments of the methods provided, friable callus from the leaf explants is induced on a callus induction medium. In some embodiments, the callus induction medium includes: a base plant medium; 1-naphthaleneacetic acid (NAA), and 6-benzylaminopurine (BAP). In certain embodiments, the base plant medium includes calcium. In another embodiment, the base plant medium further includes nitrates. In one variation, the base plant medium includes Woody Plant Medium (WPM) basal salts, Murashige and Skoog (MS) basal salts, or Driver and Kuniyuki Walnut (DKW) basal salt mixture, or any combination thereof. See Lloyd and McCown, *HortScience* 16 (1981): 453; Murashige and Skoog, *Physiologia plantarum* 15.3 (1962): 473-497; product manual of Woody Plant Medium (product code: PT026) from HiMedia Laboratories; product manual of Murashige and Skoog Plant Salt Mixture (product code: TS1004) from HiMedia Laboratories.

In some variations of the foregoing, the callus induction medium further includes: one or more vitamins, one or more sugars, L-glutamine, or myo-inositol, or any combination thereof. In certain variations, the one or more vitamins is a vitamin mixture. In another variation, the vitamin mixture includes Gamborg B-5 (B5) vitamins, or Driver and Kuniyuki Walnut (DKW) vitamins, or any combination thereof. See Gamborg et al., *Experimental cell research* 50.1 (1968): 151-158; product manual of Woody Plant Medium (product code: PT026) from HiMedia Laboratories. In another variation, the one or more sugars is sucrose.

In one variation, the callus induction medium includes: Woody Plant Medium (WPM) basal salts; Gamborg B-5 (B5) vitamins; sucrose; L-glutamine; myo-inositol; 1-naphthaleneacetic acid (NAA); and 6-benzylaminopurine (BAP).

In some variations, the NAA is at a concentration of between 0.1 mg/L and 5 mg/L; or about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.1 mg/L, about 1.2 mg/L, about 1.3 mg/L, about 1.4 mg/L, about 1.5 mg/L, about 1.6 mg/L, about 1.7 mg/L, about 1.8 mg/L, about 1.9 mg/L, about 2.0 mg/L, about 3.0 mg/L, about 4.0 mg/L, or about 5.0 mg/L.

In some variations, the BAP is at a concentration of between 0.1 mg/L and 5 mg/L; or about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.1 mg/L, about 1.2 mg/L, about 1.3 mg/L, about 1.4 mg/L, about 1.5 mg/L, about 1.6 mg/L, about 1.7 mg/L, about 1.8 mg/L, about 1.9 mg/L, about 2.0 mg/L, about 3.0 mg/L, about 4.0 mg/L, or about 5.0 mg/L.

In some variations, the L-glutamine is at a concentration of between 50 mg/L and 300 mg/L, or between 200 mg/L and 275 mg/L, or between 230 mg/L and 270 mg/L, or between 245 mg/L and 255 mg/L; or about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, or about 300 mg/L.

In some variations, the myo-inositol is at a concentration of between 10 mg/L and 200 mg/L, or between 75 mg/L and 125 mg/L, or between 90 mg/L and 110 mg/L, or between 95 mg/L and 105 mg/L; or about 10 mg/L, about 20 mg/L, about 30 mg/L, about 40 mg/L, about 50 mg/L, about 60 mg/L, about 170 mg/L, about 80 mg/L, about 90 mg/L, about 100 mg/L, about 110 mg/L, about 120 mg/L, about 130 mg/L, about 140 mg/L, about 150 mg/L, about 160 mg/L, about 170 mg/L, about 180 mg/L, about 190 mg/L, or about 200 mg/L.

In some variations, the sugar (such as, sucrose) is at a concentration of between 5 g/L and 100 g/L; or between 20 g/L and 80 g/L; or about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

It should be understood that any description of the various components in the callus induction medium described herein may be combined with each other, the same as if each and every combination were individually listed. For example, a callus induction medium including both 1-naphthaleneacetic acid (NAA) and 6-benzylaminopurine (BAP) may have, in some variations, a NAA concentration of about 1.0 mg/L and BAP concentration of 0.5 mg/L. In another variation, the NAA concentration is about 1.0 mg/L and the BAP concentration is about 1 mg/L. In yet another variation, the NAA concentration is about 1.0 mg/L and the BAP concentration is about 3.0 mg/L.

In other variations, the callus induction medium includes NAA, BAP and sucrose. In one variation of the foregoing, the NAA is at a concentration of about 1.0 mg/L, the BAP is at a concentration between 0.5 mg/L and 3 mg/L, and the sucrose is at about 30 g/L.

In yet other variations, the callus induction medium includes NAA, BAP, sucrose and L-glutamine. In one variation of the foregoing, the NAA is at a concentration of about 1.0 mg/L, the BAP is at a concentration between 0.5 mg/L and 3 mg/L, the sucrose is at about 30 g/L, and the L-glutamine is at about 250 mg/L.

In yet other variations, the callus induction medium includes NAA, BAP, sucrose, L-glutamine, and myo-inositol. In one variation of the foregoing, the NAA is at a concentration of about 1.0 mg/L, the BAP is at a concentration between 0.5 mg/L and 3 mg/L, the sucrose is at about 30 g/L, the L-glutamine is at a concentration of about 250 mg/L, and the myo-inositol is at a concentration of about 100 mg/L.

In some embodiments of the methods provided herein, the induction of friable callus is obtained after a photoperiod. The photoperiod is expressed herein as a ratio of hours of light to hours of dark; and the total hours of light and dark add up to 24 hours.

In one variation, the photoperiod is from 12:12 to 24:0, from 13:11 to 20:4, or from 14:10 to 18:6; or about 16:8.

Exposure to light can be ensured by positioning the substrates in appropriately-illuminated chambers, as is understood in the art. In some embodiments, a photosynthetic active radiation (PAR) or photosynthetic photon flux density (PPFD) of 30-240 $\mu mol/m^2 \cdot sec$, 50-200 $\mu mol/m^2 \cdot sec$, 50-190 $\mu mol/m^2 \cdot sec$, 50-180 $\mu mol/m^2 \cdot sec$, 50-170 $\mu mol/m^2 \cdot sec$, 50-160 $\mu mol/m^2 \cdot sec$, 50-150 $\mu mol/m^2 \cdot sec$, 50-100 $\mu mol/m^2 \cdot sec$, 50-90 $\mu mol/m^2 \cdot sec$, 50-80 $\mu mol/m^2 \cdot sec$, 50-70 $\mu mol/m^2 \cdot sec$, or 50-60 $\mu mol/m^2 \cdot sec$ may be used.

It should be understood that any description of the photoperiods, PAR and PPFD described herein may be combined with each other, the same as if each and every combination were individually listed. For example, in one variation, a photoperiod of 16:8 hours light:dark and a photosynthetic active radiation (PAR) or photosynthetic photon flux density (PPFD) of 50-200 $\mu mol/m^2 \cdot sec$ are employed in the methods herein.

Proliferation of Callus

In some embodiments, the induced callus is proliferated on a callus proliferation medium. In some embodiments, the callus proliferation medium includes: a base plant medium; and tidiazuron (TDZ). In certain embodiments, the base plant medium includes calcium. In another embodiment, the base plant medium further includes nitrates. In one variation, the base plant medium includes Woody Plant Medium (WPM) basal salts, Murashige and Skoog (MS) basal salts, or DKW basal salt mixture, or any combination thereof. See Lloyd and McCown, *HortScience* 16 (1981): 453; Murashige and Skoog, *Physiologia plantarum* 15.3 (1962): 473-497; product manual of Woody Plant Medium (product code: PT026) from HiMedia Laboratories; product manual of Murashige and Skoog Plant Salt Mixture (product code: TS1004) from HiMedia Laboratories.

In some variations of the foregoing, the callus proliferation medium further includes: one or more vitamins, one or more sugars, L-glutamine, or myo-inositol, or any combination thereof. In certain variations, the one or more vitamins is a vitamin mixture. In another variation, the vitamin mixture includes Gamborg B-5 (B5) vitamins, or Driver and Kuniyuki Walnut (DKW) vitamins, or any combination thereof. See Gamborg et al., *Experimental cell research* 50.1 (1968): 151-158; product manual of Woody Plant Medium (product code: PT026) from HiMedia Laboratories. In another variation, the one or more sugars include sucrose.

In one variation, the callus induction medium includes: Woody Plant Medium (WPM) basal salts; Gamborg B-5 (B5) vitamins; sucrose; L-glutamine; myo-inositol; and tidiazuron (TDZ).

In some variations, the TDZ is at a concentration of between 0.1 mg/L and 5 mg/L; or about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.1 mg/L, about 1.2 mg/L, about 1.3 mg/L, about 1.4 mg/L, about 1.5 mg/L, about 1.6 mg/L, about 1.7 mg/L, about 1.8 mg/L, about 1.9 mg/L, about 2.0 mg/L, about 2.1 mg/L, about 2.2 mg/L, about 2.3 mg/L, about 2.4 mg/L, about 2.5 mg/L, about 2.6 mg/L, about 2.7 mg/L, about 2.8 mg/L, about 2.9 mg/L, about 3.0 mg/L, about 4.0 mg/L, or about 5.0 mg/L.

In some variations, the L-glutamine is at a concentration of between 50 mg/L and 300 mg/L, or between 200 mg/L and 275 mg/L, or between 230 mg/L and 270 mg/L, or between 245 mg/L and 255 mg/L; or about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L.

In some variations, the myo-inositol is at a concentration of between 10 mg/L and 200 mg/L, or between 75 mg/L and 125 mg/L, or between 90 mg/L and 110 mg/L, or between 95 mg/L and 105 mg/L; or about 10 mg/L, about 20 mg/L, about 30 mg/L, about 40 mg/L, about 50 mg/L, about 60 mg/L, about 170 mg/L, about 80 mg/L, about 90 mg/L, about 100 mg/L, about 110 mg/L, about 120 mg/L, about 130 mg/L, about 140 mg/L, about 150 mg/L, about 160 mg/L, about 170 mg/L, about 180 mg/L, about 190 mg/L, or about 200 mg/L.

In some variations, the sugar (such as, sucrose) is at a concentration of between 5 g/L and 100 g/L; or between 20 g/L and 80 g/L; or about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

Any description of the various components in the callus proliferation medium described herein may be combined with each other, the same as if each and every combination were individually listed. For example, a callus proliferation medium including TDZ and L-glutamine may have, in some variations, a TDZ concentration between 2 mg/L and 3 mg/L, and the L-glutamine concentration between 200 mg/L and 300 mg/L.

In other variations, the callus proliferation medium includes TDZ, L-glutamine, and sucrose. In one variation of the foregoing, the TDZ is at concentration between 2 mg/L and 3 mg/L, the L-glutamine is at a concentration between 200 mg/L and 300 mg/L, and the sucrose is at a concentration between 20 g/L and 40 g/L.

In other variations, the callus proliferation medium includes TDZ, L-glutamine, sucrose, and myo-inositol. In one variation of the foregoing, the TDZ is at a concentration between 2 mg/L and 3 mg/L, the L-glutamine is at a concentration between 200 mg/L and 300 mg/L, the sucrose is at a concentration between 20 g/L and 40 g/L, and the myo-inositol is at a concentration between 50 mg/L and 150 mg/L.

Suspension of Callus

Suitable fermentation technologies known in the art developed for submerged microbial cultures may be applied in the plant suspension culture systems described herein.

In some embodiments, the proliferated callus of the present invention is suspended in a suspension medium.

In some embodiments, the suspension medium includes: a base plant medium; 2,4-dichlorophenoxyacetic acid (2,4-D); and kinetin (KIN). In certain embodiments, the base plant medium includes calcium. In another embodiment, the base plant medium further includes nitrates. In one variation, the base plant medium includes Woody Plant Medium (WPM) basal salts, Murashige and Skoog (MS) basal salts, or DKW basal salt mixture, or any combination thereof. See Lloyd and McCown, *HortScience* 16 (1981): 453; Murashige and Skoog, *Physiologia plantarum* 15.3 (1962): 473-497; product manual of Woody Plant Medium (product code: PT026) from HiMedia Laboratories; product manual of Murashige and Skoog Plant Salt Mixture (product code: TS1004) from HiMedia Laboratories.

In some variations of the foregoing, the suspension medium further includes: one or more vitamins, one or more sugars, L-glycine, or penicillin, or any combination thereof. In certain variations, the one or more vitamins is a vitamin mixture. In another variation, the vitamin mixture includes Gamborg B-5 (B5) vitamins, or Driver and Kuniyuki Walnut (DKW) vitamins, or any combination thereof. See Gamborg et al., *Experimental cell research* 50.1 (1968): 151-158; product manual of Woody Plant Medium (product code: PT026) from HiMedia Laboratories. In another variation, the one or more sugars include sucrose.

In one variation, the suspension medium includes: Murashige and Skoog (MS) basal salts; Driver and Kuniyuki Walnut (DKW) vitamins; sucrose; penicillin; 2,4-dichlorophenoxyacetic acid (2,4-D); and kinetin (KIN).

In some variations, the 2,4-dichlorophenoxyacetic acid (2,4-D) is at a concentration of between 0.1 mg/L and 5 mg/L; or about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 2.0 mg/L, about 3.0 mg/L, about 4.0 mg/L, or about 5.0 mg/L.

In some variations, the kinetin (KIN) is at a concentration of between 0.01 mg/L and 0.5 mg/L; or about 0.01 mg/L, about 0.02 mg/L, about 0.03 mg/L, about 0.04 mg/L, about 0.05 mg/L, about 0.06 mg/L, about 0.07 mg/L, about 0.08 mg/L, about 0.09 mg/L, about 0.1 mg/L, about 0.11 mg/L, about 0.12 mg/L, about 0.13 mg/L, about 0.14 mg/L, about 0.15 mg/L, about 0.16 mg/L, about 0.17 mg/L, about 0.18 mg/L, about 0.19 mg/L, about 0.2 mg/L, about 0.3 mg/L, about 0.4 mg/L, or about 0.5 mg/L.

In some variations, the L-glycine is at a concentration of between 0.5 mg/L and 5 mg/L; or about 0.5 mg/L, about 1 mg/L, about 1.5 mg/L, about 2 mg/L, about 2.5 mg/L, about 3 mg/L, about 3.5 mg/L, about 4 mg/L, or about 5 mg/L.

In some variations, the penicillin is at a concentration of between 10 mg/L and 300 mg/L; or about 10 mg/L, about 20 mg/L, about 30 mg/L, about 40 mg/L, about 50 mg/L, about 60 mg/L, about 70 mg/L, about 80 mg/L, about 90 mg/L, about 100 mg/L, about 110 mg/L, about 120 mg/L, about 130 mg/L, about 140 mg/L, about 150 mg/L, about 160 mg/L, about 170 mg/L, about 180 mg/L, about 190 mg/L, about 200 mg/L, or about 300 mg/L.

In some variations, the sugar (such as, sucrose) is at a concentration of between 5 g/L and 100 g/L; or between 20 g/L and 80 g/L; or about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

Any description of the various components in the suspension medium described herein may be combined with each other, the same as if each and every combination were individually listed. For example, when the suspension medium including both 2,4-dichlorophenoxyacetic acid (2,4-D) and kinetin (KIN) may have, in some variations, a 2,4-D concentration between 0.1 mg/L and 1 mg/L, and a KIN concentration between 0.05 mg/L and 0.5 mg/L.

In some other variations, the suspension medium includes 2,4-D, KIN and sucrose. In one variation of the foregoing, the 2,4-D is at a concentration between 0.1 mg/L and 1 mg/L, KIN is at a concentration between 0.05 mg/L and 0.5 mg/L, and the sucrose is at a concentration between 20 g/L and 40 g/L.

In other variations, the suspension medium includes 2,4-D, KIN, sucrose, and L-glycine. In one variation of the foregoing, the 2,4-D is at a concentration between 0.1 mg/L and 1 mg/L, KIN is at a concentration between 0.05 mg/L and 0.5 mg/L, the sucrose is at a concentration between 20 g/L and 40 g/L, and the L-glycine is at a concentration between 0.1 mg/L and 10 mg/L.

In other variations, the suspension medium includes 2,4-D, KIN, sucrose, L-glycine, and penicillin. In one variation of the foregoing, the 2,4-D is at a concentration between 0.1 mg/L and 1 mg/L, KIN is at a concentration between 0.05 mg/L and 0.5 mg/L, the sucrose is at a concentration between 20 g/L and 40 g/L, the L-glycine is at a concentration between 0.1 mg/L and 10 mg/L, and the penicillin is at a concentration between 10 mg/L and 300 mg/L.

Reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−10%.

It should also be understood that reference to "between" two values or parameters herein includes (and describes) embodiments that include those two values or parameters per se. For example, description referring to "between x and y" includes description of "x" and "y" per se.

Production of Secondary Metabolites

The methods described herein may be useful for producing secondary metabolites in *Theobroma*. Accordingly, in another aspect, provided herein is a method for producing a *Theobroma* secondary metabolite by: obtaining an explant from a *Theobroma* leaf; sterilizing the explant; inducing friable callus from the explant on a callus induction medium; proliferating the transformed friable callus on a callus proliferation medium; suspending the proliferated callus in a suspension medium; and recovering a secondary metabolite from the suspension medium. In some variations of the foregoing aspect, any of the variations of the callus induction medium, callus proliferation medium, and suspension medium described herein may be used in the method.

Secondary metabolism refers to the biological pathways that are not absolutely required for the survival of the organism. A metabolic pathway in secondary metabolism is referred to as a "secondary metabolic pathway". Compounds such as substrates, intermediates and products of secondary metabolic pathways are accordingly referred to as "secondary metabolites". Examples of plant secondary metabolites include phenols, flavonoids, tannins, alkaloids, steroids, terpenes, etc. Examples of secondary metabolites found in *Theobroma* include methylxanthines such as theobromine and caffeine. In some embodiments, the secondary metabolite is a phenol, a flavonoid, a methylxanthine, or a fatty acid.

Suitable fermentation technologies known in the art developed for submerged microbial cultures may be applied in the plant suspension culture systems described herein to produce plant secondary metabolites.

The *Theobroma* secondary metabolites may be processed into, or contribute to the taste and/or flavor of, a *Theobroma* product. *Theobroma* products include, for example, cocoa liquor, chocolate, compound chocolate, chocolate-like substance, cocoa powder, and cocoa butter.

In some variations, the method for producing a *Theobroma* secondary metabolite further comprises transforming the induced callus with an expressible transgene that encodes a product in the biosynthetic pathway of the secondary metabolite. In some embodiments, the transgene encodes an enzyme that synthesizes the secondary metabolite. In some embodiments, the transgene encodes an enzyme that synthesizes a precursor to the secondary metabolite. In some embodiments, the transgene encodes a gene product that inhibits the degradation of the secondary metabolite. Suitable transformation techniques include, for example, transfection with viral vectors; transformation with plasmid vectors; electroporation; microinjection; *Agrobacterium*-mediated transfer; direct DNA uptake; Whiskers-mediated transformation; and microprojectile bombardment. Methods for transforming plant cells, plants and portions thereof are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London. In some embodiments, the transformation is achieved by particle bombardment or by *Agrobacterium* mediation.

Production of Virus Particles

In certain embodiments, the methods described herein may be useful for isolating and analyzing virus particles related to infectious diseases in *Theobroma*. In some embodiments, the methods described herein further include co-cultivating the cell suspension with one or more viruses. In some embodiments, the one or more viruses comprise the cacao swollen shoot virus (CSSV) which is the pathogen responsible for the cacao swollen shoot disease.

CSSV is a plant pathogenic virus of the family Caulimoviridae that primarily infects cacao trees. CSSV can decrease cacao yield within the first year of infection, and usually kills the tree within a few years. Symptoms vary by strain, but leaf discoloration, stem/root swelling, and die-back generally occur. The virus is transmitted from tree to tree by mealybug vectors. The methods and media disclosed in this invention thus may facilitate insolation and characterization of CSSV and management of the cacao swollen shoot disease.

EXAMPLES

The following examples are offered to illustrate provided embodiments and are not intended to limit the scope of the present disclosure.

Example 1

Establishment of Cacao Cell Suspension Using Leaf Explants

This Example demonstrates the establishment of cacao cell suspension using leaves as donor explants.

One- or two-year-old *Theobroma cacao* plants were selected and used as donor material to collect young leaves as explants for callus formation. The second youngest leaves with quick greening color (Classified as stage Il by Greathouse et al., *American journal of botany* 58.4 (1971): 281-286) were selected and harvested for in vitro culture (FIG. 1).

The leaves were cleaned with soap and rinsed with distilled sterile water for three times. Afterwards, the leaves were cut in pieces in sizes of 2 cm$^2$, disinfected by immersion in alcohol 70% for five minutes, and rinsed three times with ultrapure sterile water. Then, the leaf explants were immersed in 1% calcium hypochlorite or 20% sodium hypochlorite for 50-60 minutes in vacuum condition (70 k-pascal) and rinsed 3-5 times with ultrapure sterile water.

After disinfection, the sterile leaves were cut into pieces of 1 cm$^2$ in a chamber flow laminar in aseptic condition, and placed into Petri dishes with 30 mL of solid callus induction medium (CIM) (Table 1) for a month. After this period of culture, the leaves explants were transferred immediately to solid callus proliferation medium (CPM) (Table 2) for 8 weeks, with transferences every 2-3 weeks until callus were proliferated in abundance. The cultures were incubated in a photoperiod of 16 h light: 8 h dark, with temperatures at 27±2° C.

TABLE 1

Callus Induction Medium (CIM)

| Medium components | Concentration |
| --- | --- |
| Woody Plant Medium (WPM) salts | 50%[a] |
| Gamborg B-5 (B5) vitamins | 1 ml/L |
| L-glutamine | 250 mg/L |
| Myo-inositol | 100 mg/L |
| Sucrose | 30 g/L |
| 1-naphthaleneacetic acid (NAA) | 1.0 mg/L |
| 6-benzylaminopurine (BAP) | 0.5-3.0 mg/L |

[a]100% of the component in the medium refers to the use of the formula for 1 liter of solution as is described in the product manual of Woody Plant Medium (product code: PT026) from HiMedia Laboratories.

TABLE 2

Callus Proliferation Medium (CPM)

| Medium components | Concentration |
| --- | --- |
| Woody Plant Medium (WPM) salts | 100%[a] |
| Gamborg B-5 (B5) vitamins | 1 ml/L |
| L-glutamine | 250 mg/L |
| Myo-inositol | 100 mg/L |

TABLE 2-continued

Callus Proliferation Medium (CPM)

| Medium components | Concentration |
| --- | --- |
| Sucrose | 30 g/L |
| Tidiazuron (TDZ) | 2.2 mg/L |

[a]100% of the component in the medium refers to the use of the formula for 1 liter of solution as is described in the product manual of Woody Plant Medium (product code: PT026) from HiMedia Laboratories.

After that, 500-1000 mg of the friable callus were transferred into 250 ml flasks with 30 mL of liquid suspension medium (SUM, Table 3) with 500 mg/L of pectinase for 4 weeks, with the medium refreshed every week (allow the cells to settle and remove 20 mL of supernatant of old medium and add 20 mL of new medium). Then, the cell suspensions were refreshed in SUM medium without pectinase every week for 2-6 months. The cultures in liquid medium were incubated in dark, with temperatures at 27±2° C. placed in a shaker at 120 rpm.

TABLE 3

Suspension Medium (SUM)

| Medium components | Concentration |
| --- | --- |
| Murashige and Skoog (MS) salts | 100%[a] |
| Driver and Kuniyuki Walnut (DKW) vitamins | 1 ml/L |
| L-glycine | 2 mg/L |
| Sucrose | 30 g/L |
| Penicillin | 100 mg/L |
| 2.4-D (2,4-dichlorophenoxyacetic acid) | 0.5 mg/L |
| Kinetin (KIN) | 0.1 mg/L |

[a]100% of the component in the medium refers to the use of the formula for 1 liter of solution as is described in the product manual of Murashige and Skoog Plant Salt Mixture (product code: TS1004) from HiMedia Laboratories.

Example 2

Leaf Disinfection

This Example explores the factors affecting leaf disinfection in the establishment of cacao cell suspension cultures.

Figure 2:
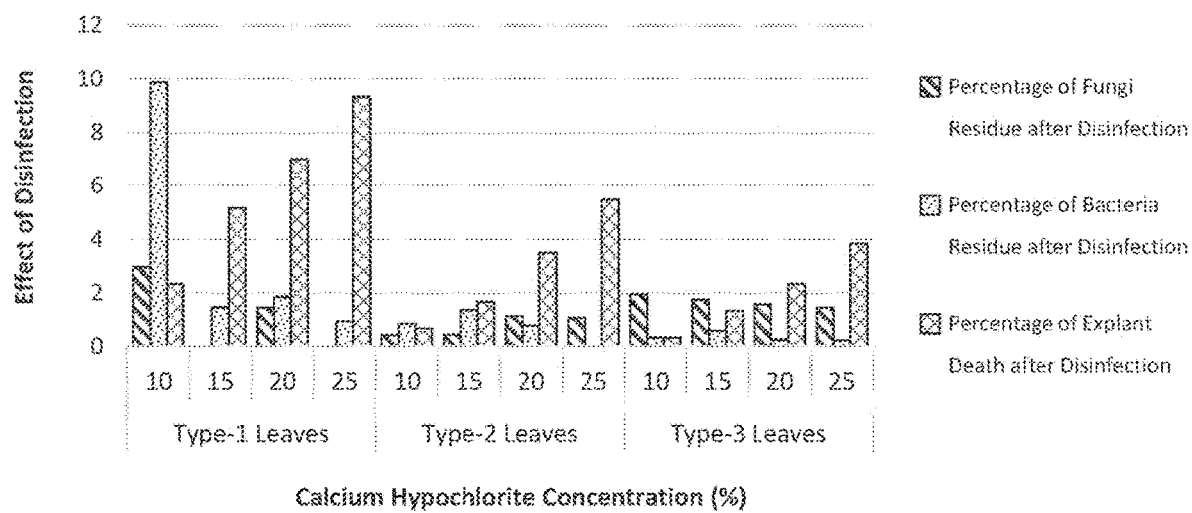
FIG. 2 shows effects of disinfection in type-1, type-2, and type-3 leaves (for leaf type characterization, see Greathouse et al., *American journal of botany* 58.4 (1971): 281-286).
Figure 3:
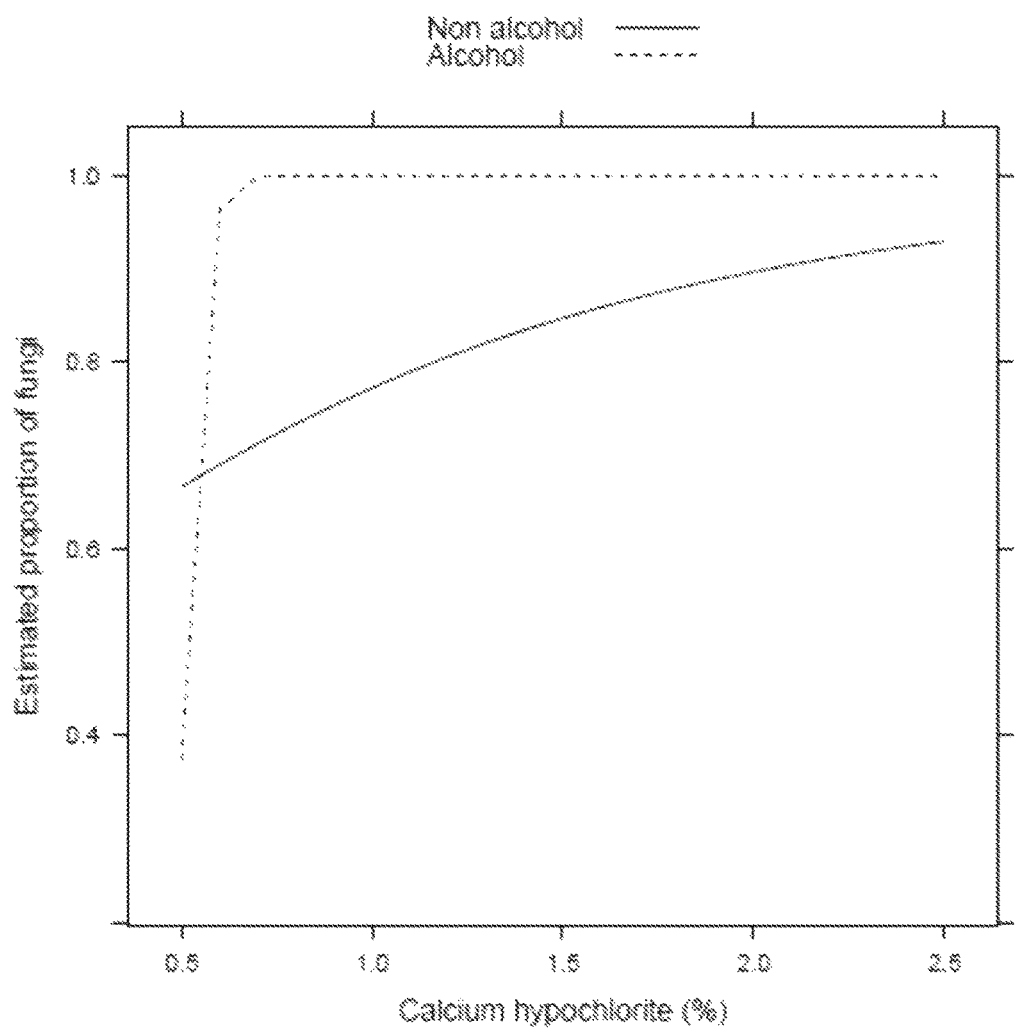
FIG. 3 shows disinfecting effects of calcium hypochlorite and alcohol in eliminating fungi on leaf explants.
Figure 4:
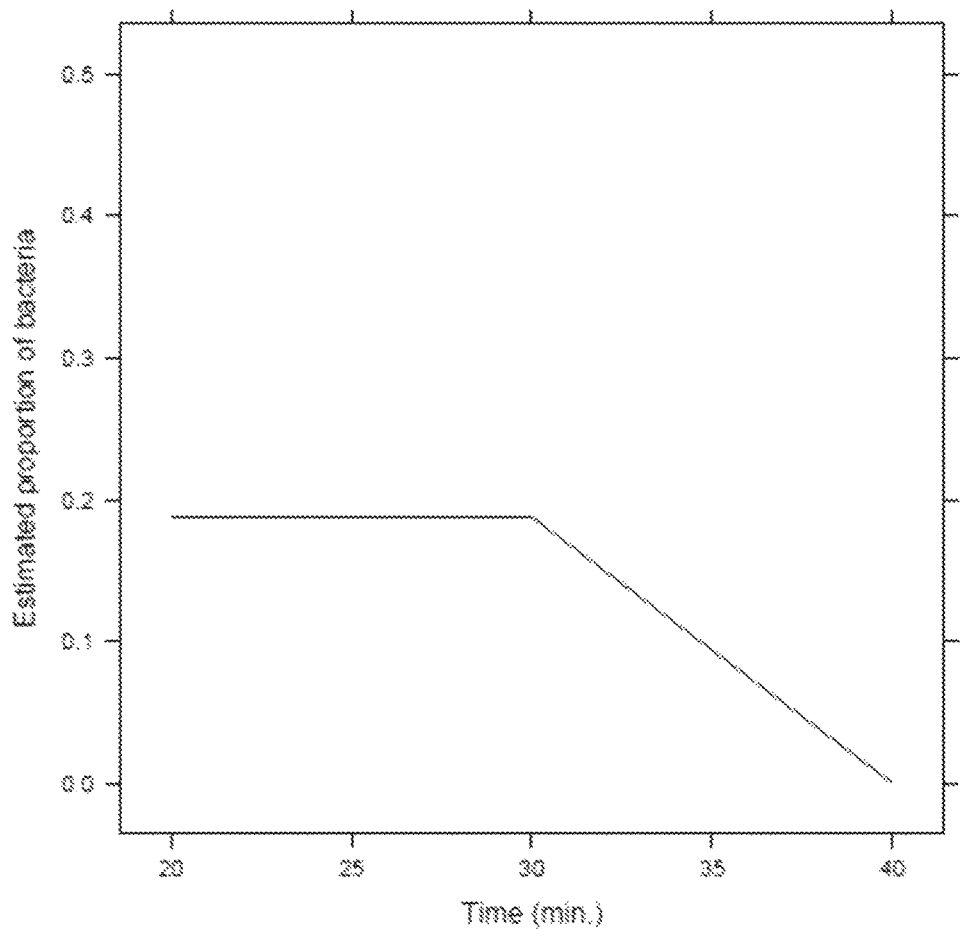
FIG. 4 shows disinfecting effects of calcium hypochlorite and alcohol in eliminating bacteria on leaf explants.

FIG. 2 shows that the best type of leave to induce callus formation is type 2 leaves. However, due to a high percentage of leaf death after the use of high concentration of calcium hypochlorite, an experiment was devised to use a low concentration of calcium hypochlorite as a treatment with vacuum for a period of time (FIGS. 3 and 4; Tables 4 and 5). It was found that a low concentration of calcium hypochlorite (0.5 mg/L) for 40 minutes was the best treatment for cacao leaf disinfection.

TABLE 4

Deviance analysis for presence of fungi

| | Df | Deviance | Resid. Df | Resid. Dev | Pr(>Chi) |
| --- | --- | --- | --- | --- | --- |
| Null | | | 47 | 49.13 | |
| Hypochlorite | 1 | 9.35 | 46 | 39.78 | 0.0022 |
| Treatment with alcohol | 1 | 0.00 | 45 | 39.78 | 1.0000 |
| Treatment with fungicide | 1 | 0.00 | 44 | 39.78 | 1.0000 |
| Time | 1 | 0.61 | 43 | 39.16 | 0.4330 |
| Hypochlorite: treatment with alcohol | 1 | 11.46 | 42 | 27.70 | 0.0007 |
| Hypochlorite: treatment with fungicide | 1 | 3.61 | 41 | 24.10 | 0.0576 |

TABLE 4-continued

Deviance analysis for presence of fungi

| | Df | Deviance | Resid. Df | Resid. Dev | Pr(>Chi) |
|---|---|---|---|---|---|
| Treatment with alcohol: treatment with fungicide | 1 | 0.56 | 40 | 23.54 | 0.4554 |
| Treatment with alcohol: time | 1 | 0.00 | 39 | 23.54 | 1.0000 |
| Hypochlorite: treatment with alcohol: treatment with fungicide | 1 | 0.00 | 38 | 23.54 | 0.9998 |

TABLE 5

Deviance analysis for presence of bacteria

| | Df | Deviance | Resid. Df | Resid. Dev | Pr(>Chi) |
|---|---|---|---|---|---|
| Null | | | 47 | 36.17 | |
| Hypochlorite | 1 | 1.54 | 46 | 34.63 | 0.2145 |
| Treatment with alcohol | 1 | 9.46 | 45 | 25.17 | 0.0021 |
| Treatment with fungicide | 1 | 0.98 | 44 | 24.18 | 0.3218 |
| Time | 1 | 4.10 | 43 | 20.09 | 0.0430 |
| Hypochlorite: treatment with alcohol | 1 | 0.00 | 42 | 20.09 | 1.0000 |
| Hypochlorite: treatment with fungicide | 1 | 0.00 | 41 | 20.09 | 1.0000 |
| Treatment with alcohol: treatment with fungicide | 1 | 0.00 | 40 | 20.09 | 1.0000 |
| Treatment with alcohol: time | 1 | 0.00 | 39 | 20.09 | 0.9998 |
| Hypochlorite: treatment with alcohol: treatment with fungicide | 1 | 0.00 | 38 | 20.09 | 1.0000 |

Example 3

Effects of Hormones and Photoperiod on Callus Induction

This Example demonstrates the effects of hormones and photoperiod on callus induction in the establishment of cacao cell suspension cultures.

Figure 5:
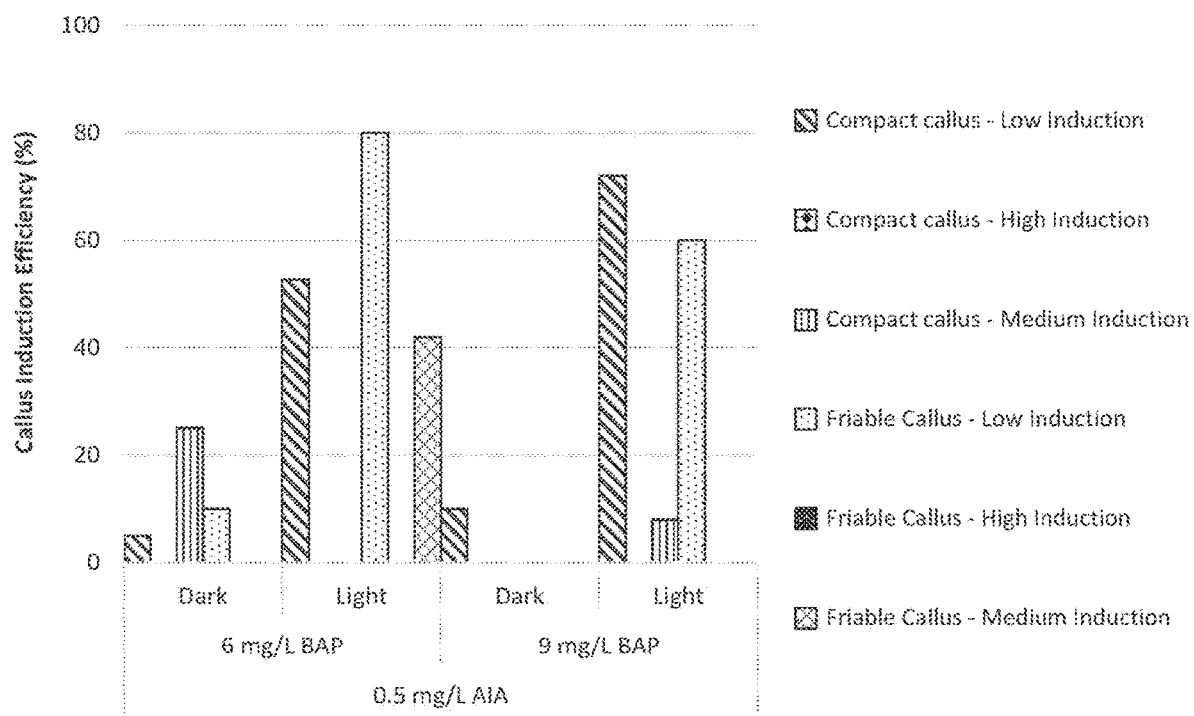
FIG. 5 shows effects of hormone balance of BAP/AIA and photoperiod conditions on callus formation.
Figure 6:
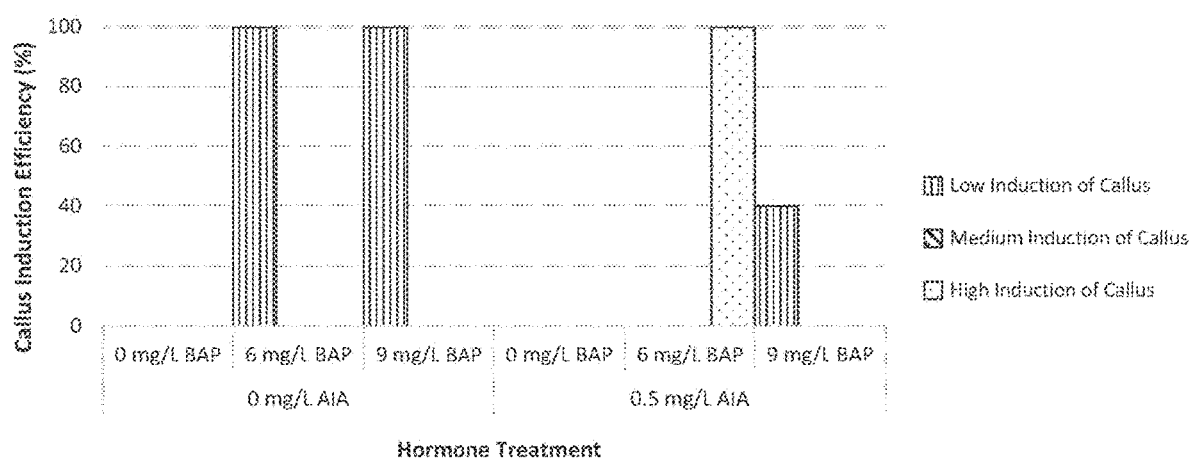
FIG. 6 shows effects of hormone balance of BAP/AIA on callus formation.
Figure 7:
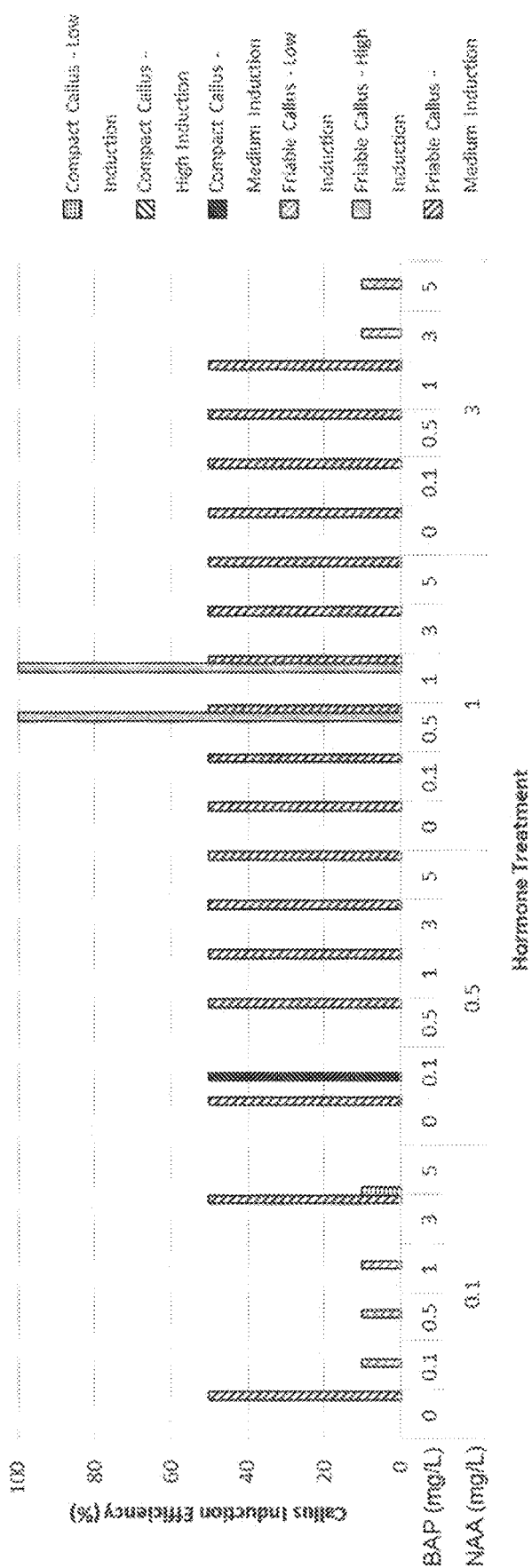
FIG. 7 shows effects of hormone balance of BAP/NAA on callus formation.

The screening of a set of plant growth hormones led to the combination of 1-naphthaleneacetic acid (NAA) and 6-benzylaminopurine (BAP) in the use of callus induction medium. FIGS. 5 and 6 show results of the combination of BAP and indole acetic acid (IAA), and FIG. 7 shows the results of the combination of NAA with BAP. It was found that NAA at 1 mg/L in combination with BAP at 0.5-3 mg/L surprisingly induced friable callus formation in desirable quantity. Other combinations of plant hormones yielded calluses in inferior quality (i.e. compact callus, which is not suitable for establishing cell suspension cultures) and/or in too low of a quantity for establishing cell suspension cultures. Without wishing to be bound by any theories, the combination of NAA and BAP is thought to be important for induction of friable callus for establishment of cacao cell suspension cultures.

FIG. 5 also shows the results of using light in culture incubation. It was found that efficiency of friable callus formation was high when cultures were incubated in a photoperiod of 16 h light: 8 h dark.

What is claimed is:

1. A method for preparing a *Theobroma* cell suspension culture, comprising:
   obtaining an explant from a young *Theobroma* leaf, wherein the *Theobroma* is *Theobroma cacao;*
   sterilizing the explant;
   inducing friable callus from the explant on a callus induction medium, wherein the callus induction medium comprises:
      a base plant medium;
      1-naphthaleneacetic acid (NAA) at a concentration of 1 mg/L; and
      6-benzylaminopurine (BAP) at a concentration from 0.5 mg/L to 1 mg/L;
   proliferating the induced callus on a callus proliferation medium, wherein the callus proliferation medium comprises: the base plant medium and tidiazuron, and
   wherein the base plant medium comprises:
      woody plant medium salts;
      vitamins;
      L-glutamine;
      myo-inositol; and
      sucrose; and
   suspending the proliferated callus in a suspension medium, wherein the suspension medium comprises:
      salts;
      vitamins;
      L-glycine;
      sucrose;
      penicillin;
      2,4-dichlorophenoxyacetic acid (2,4-D); and
      kinetin.

2. The method of claim 1, wherein the sterilization comprises contacting the explant in a hypochlorite solution under vacuum condition.

3. The method of any one of claim 1, wherein the induction of friable callus is obtained after a photoperiod of 16 hours of light and 8 hours of dark.

4. A *Theobroma* cell suspension culture produced by the method of any one of claim 1.

5. A method for producing a *Theobroma* secondary metabolite, comprising:
   obtaining an explant from a young *Theobroma* leaf, wherein the *Theobroma* is *Theobroma cacao;* sterilizing the explant;
inducing friable callus from the explant on a callus induction medium, wherein the callus induction medium comprises:
  a base plant medium;
  1-naphthalene acetic acid (NAA) at a concentration of 1 mg/L; and
  6-benzylaminopurine (BAP) at a concentration from 0.5 mg/L to 1 mg/L;
proliferating the transformed friable callus on a callus proliferation medium,
  wherein the callus proliferation medium comprises: the base plant medium and tidiazuron, and
  wherein the base plant medium comprises:
  woody plant medium salts;
  vitamins;
  L-glutamine;
  myo-inositol; and
  sucrose;
suspending the proliferated callus in a suspension medium, wherein the suspension medium comprises:
  salts;
  vitamins;
  L-glycine;
  sucrose;
  penicillin;
  2,4-dichlorophenoxyacetic acid (2,4-D); and
  kinetin (KIN); and
recovering a secondary metabolite from the suspension medium.

6. The method of claim 5, further comprising transforming the induced callus with an expressible transgene that encodes a product in the biosynthetic pathway of the secondary metabolite.

7. The method of claim 6, wherein the transformation is achieved by particle bombardment or by *Agrobacterium* mediation.

8. The method of any one of claim 5, wherein the secondary metabolite is a phenol, a flavonoid, a methylxanthine, or a fatty acid.

9. The method of any one of claim 5, wherein the sterilization comprises contacting the explant in a hypochlorite solution under vacuum.

10. The method of any one of claim 5, wherein the induction of friable callus is obtained after a photoperiod of 16 hours of light and 8 hours of dark.

11. A *Theobroma* secondary metabolite produced by the method of any one of claim 5.

12. A callus induction medium for inducing friable callus from *Theobroma* leaf explants, wherein the *Theobromao* is *Theobroma cacao* comprising:
  a base plant medium;
  1-naphthaleneacetic acid (NAA) at a concentration of 1 mg/L, and
  6-benzylaminopurine (BAP) at a concentration from 0.5 mg/L to 5 mg/L.

13. A callus proliferation medium for proliferating friable callus induced from *Theobroma* leaf explants, wherein the *Theobroma* is *Theobroma cacao*, comprising:
  a base plant medium wherein the base plant medium comprises:
  woody plant medium salts;
  vitamins;
  L-glutamine;
  myo-inositol; and
  sucrose; and
  optionally one or more vitamins; and
  tidiazuron (TDZ) at a concentration from 1 mg/L to 5 mg/L.

* * * * *